United States Patent
Schlam et al.

(10) Patent No.: US 8,691,981 B2
(45) Date of Patent: Apr. 8, 2014

(54) CRYSTALLINE FORMS OF (S)-1-(4-(5-CYCLOPROPYL-1H-PYRAZOL-3-YLAMINO)PYRROLO[1,2-F][1,2,4]TRIAZIN-2-YL)-N-(6-FLUOROPYRIDIN-3-YL)-2-METHYLPYRROLIDINE-2-CARBOXAMIDE

(75) Inventors: Roxana Schlam, East Brunswick, NJ (US); Alicia Tee Fuay Ng, East Haven, CT (US); Chenkou Wei, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/576,973

(22) PCT Filed: Feb. 3, 2011

(86) PCT No.: PCT/US2011/023521
§ 371 (c)(1),
(2), (4) Date: Aug. 3, 2012

(87) PCT Pub. No.: WO2011/097331
PCT Pub. Date: Aug. 11, 2011

(65) Prior Publication Data
US 2012/0302571 A1  Nov. 29, 2012

Related U.S. Application Data

(60) Provisional application No. 61/300,923, filed on Feb. 3, 2010.

(51) Int. Cl.
*C07D 487/04* (2006.01)
*C07D 401/14* (2006.01)
*A61K 31/53* (2006.01)
*A61P 35/00* (2006.01)

(52) U.S. Cl.
USPC .......................................... 544/183; 514/243

(58) Field of Classification Search
USPC .......................................... 544/183; 514/243
See application file for complete search history.

(56) References Cited

U.S. PATENT DOCUMENTS

| 7,534,792 B2 | 5/2009 | Wittman et al. |
| 7,879,855 B2 | 2/2011 | Wittman et al. |
| 8,263,765 B2 | 9/2012 | Wittman et al. |
| 2012/0302747 A1 | 11/2012 | Wittman et al. |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4*
Dermer et al., Bio/Technology, 1994, 12:320.*
Piccaluga et al., Expert Opinion in Biological Therapy, 7(10), 1597-1611,2007.*
Golub et al., Science, 286, 531-537, 1999.*
Cecil Textbook of Medicine, edited by Bennet, J.C., and Plum F., 20th edition,vol. 1, 1004-1010, 1996.*
International Search Report issued Aug. 7, 2012.
Wittman, Mark D., et al., "Discovery of a 2,4-Disubstituted Pyrrolo-[1,2-f][1,2,4]triazine Inhibitor (BMS-754807) of Insulin-like Growth Factor Receptor (IGF-1R) Kinase in Clinical Development," J. Med. Chem. 2009, vol. 52, pp. 7360-7363.
Caira, M.R., "Crystalline Polymorphism of Organic Compounds," Topics in Current Chemistry, vol. 198, pp. 163-208 , 1998.

* cited by examiner

*Primary Examiner* — Venkataraman Balasubramanian
(74) *Attorney, Agent, or Firm* — Elliott Korsen

(57) ABSTRACT

Crystalline forms of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide of the formula (I) are provided. Also provided is a pharmaceutical composition comprising one or more crystalline forms of (3R,4R)-4-amino-1-[[4-[(3-methoxyphenyl)amino]pyrrolo[2,1-f][1,2,4]triazin-5-yl]methyl]piperidin-3-ol, as well as a method of using one or more crystalline forms of (3R,4R)-4-amino-1-[[4-[(3-methoxyphenyl)amino]pyrrolo[2,1-f][1,2,4]triazin-5-yl]methyl]piperidin-3-ol in the treatment of cancer and other proliferative diseases.

11 Claims, 9 Drawing Sheets

PXRD of N-1

(I)

PXRD of N-2

PXRD of N-1/N-2

DSC of N-1

DSC of N-2

TGA of N-1

TGA of N-2

Carbon-13 ssNMR Spectrum of N-1

Carbon-13 ssNMR Spectrum of N-2

CRYSTALLINE FORMS OF (S)-1-(4-(5-CYCLOPROPYL-1H-PYRAZOL-3-YLAMINO)PYRROLO[1,2-F][1,2,4]TRIAZIN-2-YL)-N-(6-FLUOROPYRIDIN-3-YL)-2-METHYLPYRROLIDINE-2-CARBOXAMIDE

FIELD OF THE INVENTION

The present invention generally relates to crystalline forms of the methane sulfonic acid (MSA) salt of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide. The present invention also relates to a pharmaceutical composition comprising a crystalline form of the MSA salt of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide, as well as a method of using a crystalline form of the MSA salt of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide in the treatment of cancer and other proliferative diseases.

BACKGROUND OF THE INVENTION

The invention relates to crystalline forms of a compound which inhibits tyrosine kinase enzymes, compositions which contain the tyrosine kinase inhibiting compound and methods of using the crystalline form of inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders.

Tyrosine kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

(S)-1-(4-(5-Cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide, has the structure of formula I:

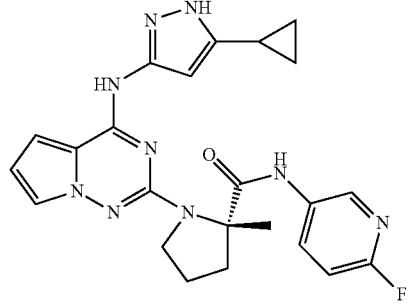

(I)

and is referred to herein as "Compound I". Compound I is an insulin-like growth factor receptor inhibitor, (IGF-1R), thereby making it useful as an anti-cancer agent. Compound I and methods of synthesizing the compound are disclosed in U.S. Pat. No. 7,534,792, which is assigned to the present assignee and is incorporated herein by reference in its entirety.

Typically, in the preparation of a pharmaceutical composition, a form of the active ingredient is sought that has a balance of desired properties such as dissolution rate, solubility, bioavailability, and/or storage stability. For example, it is desired that a form of the active ingredient, which has the requisite solubility and bioavailability, also has sufficient stability that it does not convert during manufacture or storage of the pharmaceutical composition to a different form, which has different solubility and/or bioavailability. One or more forms of Compound I are desired having properties and stability that allow the preparation of pharmaceutical compositions suitable for the treatment of diseases such as cancer. Further, one or more forms of Compound I are desired that allow the isolation and/or purification of Compound I, for example, during a preparative process.

The PXRD patterns of N-1 and N-2 bulk materials of the forms isolated display many similarities, but are easily distinguished by a few unique low angle peaks. Where one form has peaks, the other form has baseline and vice versa. In fact, these materials display a whole range of patterns with variable peak heights and widths mainly at low angle. Additionally, slurries of polymorphic mixtures of a compound are expected to convert to a single form. In this case, during the determination of the thermodynamic relationships of the forms, it was noted that slurries containing both forms are sluggish to convert to the more stable form.

It has been found through extensive testing of the forms isolated that the phase purity is not expected to have significant impact on the performance of drug product, due to the close structural and potentially thermodynamic relationships between N-1 and N-2 of the 1:1 MSA salt. Thus, a crystalline material with PXRD characteristics of N-1 and/or N-2 was chosen and will be referred to as N-1/N-2.

SUMMARY OF THE INVENTION

A first aspect of the present invention provides a crystalline form of the MSA salt of Compound I:

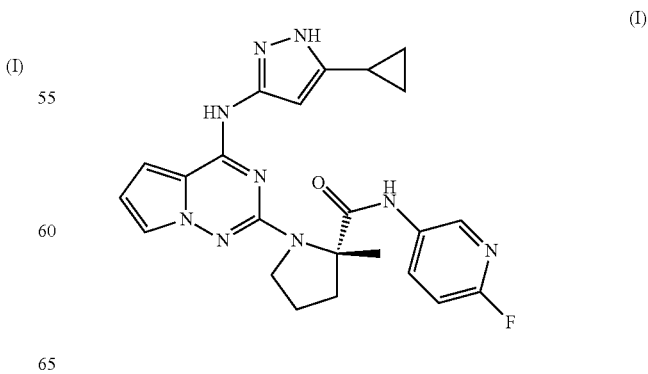

(I)

comprising Form N-1.

A second aspect of the present invention provides a crystalline form of the MSA salt of Compound I comprising Form N-2.

A third aspect of the present invention provides a crystalline form of the MSA salt of Compound I comprising a crystalline material with PXRD characteristics of Form N-1 and/or Form N-2.

A further aspect of the invention provides a pharmaceutical composition comprising one or more of Form N-2 and/or Form N-1 of the MSA salt of Compound I, and a pharmaceutically acceptable carrier or diluent.

Another aspect of the present invention provides a method for treating cancer, comprising administering to a mammalian species in need thereof, a therapeutically effect amount of the MSA salt of Compound I, wherein Compound I MSA salt is a crystalline material with PXRD characteristics of N-1 and/or N-2.

The names used herein to characterize a specific form, e.g., "N-1" etc., should not be considered limiting with respect to any other substance possessing similar or identical physical and chemical characteristics, but rather it should be understood that these designations are mere identifiers that should be interpreted according to the characterization information also presented herein.

BRIEF DESCRIPTION OF THE DRAWINGS

The invention is illustrated by reference to the accompanying drawings described below.

DETAILED DESCRIPTION OF THE INVENTION

Figure 1:
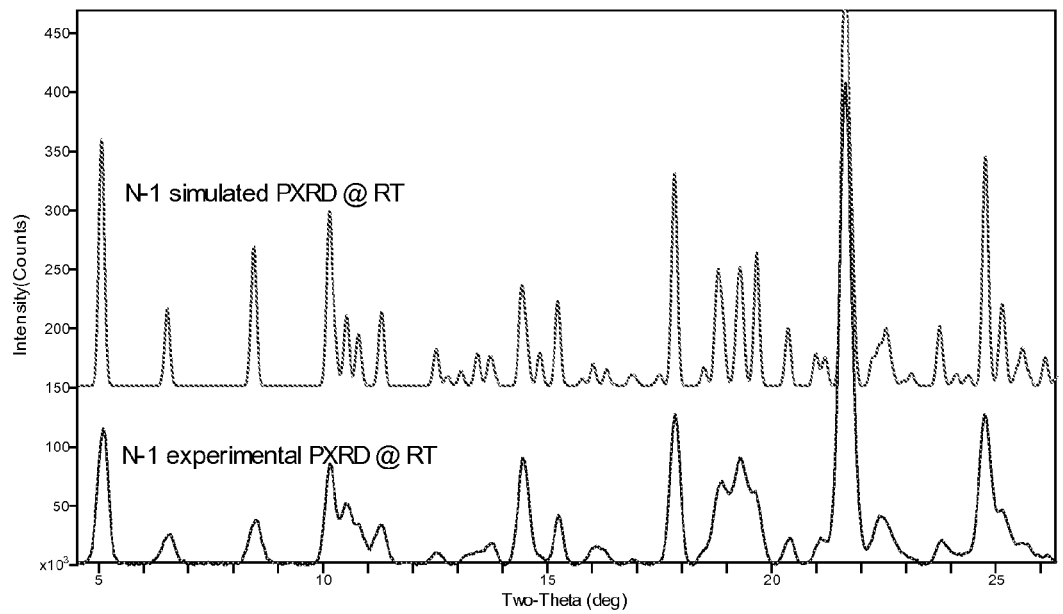
FIG. 1 shows experimental (at room temperature) and simulated (at T=25°) powder x-ray diffraction patterns (CuKα λ=1.5418 Å) of the N-1 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.
Figure 1:
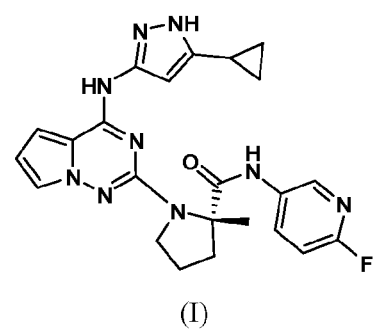

As used herein, "polymorphs" refer to crystalline forms having the same chemical compositions but different spatial arrangements of the molecules and/or ions forming the crystals.

As used herein, "amorphous" refers to a solid form of a molecule and/or ions that is not crystalline. An amorphous solid does not display a definitive X-ray diffraction pattern with sharp maxima.

As used herein, "substantially pure," when used in reference to a crystalline form, means a sample of the crystalline form of the compound having a purity greater than 90 weight %, including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of Compound I MSA salt may be deemed substantially pure in that it has a purity greater than 90 weight % of the crystalline form of Compound IMSA salt, as measured by means that are at this time known and generally accepted in the art, where the remaining less than 10 weight % of material comprises other form(s) of Compound I MSA salt and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the parameter "molecules/asymmetric unit" refers to the number of molecules of Compound I MSA salt in the asymmetric unit.

As used herein, the unit cell parameter "molecules/unit cell" refers to the number of molecules of Compound IMSA salt in the unit cell.

When dissolved, the crystalline form of Compound IMSA salt loses its crystalline structure, and is therefore referred to as a solution of Compound I. One or more of the crystalline forms of Compound I MSA salt disclosed herein, may be used for the preparation of liquid formulations in which the compound is dissolved or suspended.

A therapeutically effective amount of crystalline Form N-1 and/or Form N-2 of Compound I MSA salt may be combined with a pharmaceutically acceptable carrier or diluent to provide pharmaceutical compositions of this invention. By "therapeutically effective amount", it is meant an amount that, when administered alone or an amount when administered with an additional therapeutic agent, is effective to prevent, suppress, or ameliorate a disease or condition or the progression of a disease or condition.

The present invention provides crystalline forms of the MSA salt of Compound I:

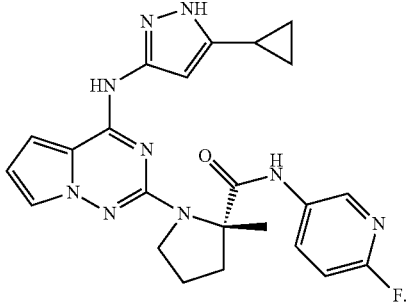

(I)

The first aspect of the invention provides the MSA salt of a neat crystalline form of Compound I MSA salt and is referred herein as the "Form N-1" or "N-1 Form".

In one embodiment, this form is characterized by unit cell parameters approximately equal to the following:
Cell dimensions:
a=16.3032 Å
b=9.5960 Å
c=18.0141 Å
α=90.0°
β=104.814°
γ=90.0°
Space group: $P2_1$
Molecules of Compound I/asymmetric unit: 2
Volume=2724.6 Å$^3$
Density (calculated)=1.359 g/cm$^3$
wherein measurement of the crystalline form is at a temperature of about 25° C.

In a different embodiment, this form of Compound I MSA salt is characterized by the simulated powder x-ray diffraction pattern substantially in accordance with that shown in FIG. 1 and/or by the observed powder x-ray diffraction pattern substantially in accordance with that shown in FIG. 1.

In another embodiment, there is disclosed the N-1 Form of Compound I MSA salt with characteristic peaks in a powder X-ray diffraction pattern at values of 2θ (CuKα λ=1.5418 Å at a temperature of about 25° C.) of 5.1±0.1, 6.5±0.1, 8.5±0.1, 10.1±0.1, 10.5±0.1, 11.3±0.1, 14.4±0.1, 15.2±0.1, 17.8±0.1, 19.7±0.1, 21.6±0.1, wherein measurement of the crystalline form is at a temperature of about 25° C. Characteristic diffraction peak positions (degrees 2θ±0.1) @ RT are based on a high quality pattern collected with a diffractometer (CuKα) with a spinning capillary and 2θ calibrated with a NIST (National Institute of Standards and Technology) or other suitable standard.

In a further embodiment, this form of Compound I MSA salt is characterized by the fractional atomic coordinates substantially as listed in Table 1.

TABLE 1

Fractional Atomic Coordinates for the MSA salt Form N-1 at T = RT

| Atom | X | Y | Z |
|---|---|---|---|
| S1 | 0.5514 | 0.6022 | 0.0991 |
| F1 | −0.3171 | 1.2963 | 0.6096 |
| N1 | −0.2015 | 1.1871 | 0.6805 |
| N2 | −0.1130 | 0.8398 | 0.6710 |
| N3 | 0.0070 | 0.6339 | 0.7357 |
| N4 | 0.1345 | 0.7333 | 0.8007 |
| N5 | 0.0842 | 0.7561 | 0.6658 |
| N6 | 0.1567 | 0.8328 | 0.6715 |
| N7 | 0.2511 | 0.8470 | 0.8755 |
| N8 | 0.1826 | 0.7045 | 0.9495 |
| N9 | 0.1910 | 0.6900 | 1.0259 |
| O1 | −0.1375 | 0.7281 | 0.5567 |
| O2 | 0.4939 | 0.4977 | 0.1088 |
| O3 | 0.5642 | 0.7053 | 0.1577 |
| O4 | 0.6308 | 0.5537 | 0.0903 |
| C1 | 0.5055 | 0.6864 | 0.0124 |
| C2 | 0.3562 | 0.7648 | 1.2003 |
| C3 | 0.3101 | 0.8945 | 1.1959 |
| C4 | 0.2674 | 0.7740 | 1.1531 |
| C5 | 0.2500 | 0.7731 | 1.0683 |
| C6 | 0.2838 | 0.8458 | 1.0182 |
| C7 | 0.2393 | 0.7997 | 0.9458 |
| C8 | 0.2014 | 0.8181 | 0.8068 |
| C9 | 0.2150 | 0.8727 | 0.7382 |
| C10 | 0.2742 | 0.9573 | 0.7174 |
| C11 | 0.2505 | 0.9651 | 0.6379 |
| C12 | 0.1776 | 0.8889 | 0.6101 |
| C13 | 0.0758 | 0.7075 | 0.7319 |
| C14 | −0.0001 | 0.5572 | 0.8044 |
| C15 | −0.0740 | 0.4579 | 0.7738 |
| C16 | −0.1256 | 0.5260 | 0.7032 |
| C17 | −0.0618 | 0.6012 | 0.6655 |
| C18 | −0.0318 | 0.5072 | 0.6102 |
| C19 | −0.1051 | 0.7282 | 0.6260 |
| C20 | −0.1669 | 0.9562 | 0.6485 |
| C21 | −0.1524 | 1.0746 | 0.6932 |
| C22 | −0.2676 | 1.1807 | 0.6218 |
| C23 | −0.2895 | 1.0688 | 0.5732 |
| C24 | −0.2393 | 0.9541 | 0.5863 |
| S1' | 0.0068 | 0.4919 | 0.0962 |
| F1' | 0.4678 | 0.2728 | 0.4192 |
| N1' | 0.4876 | 0.4104 | 0.3269 |
| N2' | 0.5753 | 0.7601 | 0.3247 |
| N3' | 0.6435 | 0.9671 | 0.2454 |
| N4' | 0.7372 | 0.8658 | 0.1836 |
| N5' | 0.7626 | 0.8546 | 0.3193 |
| N6' | 0.8318 | 0.7765 | 0.3164 |
| N7' | 0.8157 | 0.7532 | 0.1122 |
| N8' | 0.6993 | 0.8813 | 0.0354 |
| N9' | 0.6656 | 0.8942 | −0.0418 |
| O1' | 0.6042 | 0.8991 | 0.4298 |
| O2' | −0.0676 | 0.5669 | 0.0896 |
| O3' | 0.0178 | 0.3913 | 0.1564 |
| O4' | 0.0793 | 0.5745 | 0.1022 |
| C1' | −0.0069 | 0.4042 | 0.0098 |
| C2' | 0.7230 | 0.7491 | −0.2147 |
| C3' | 0.7322 | 0.8975 | −0.2116 |
| C4' | 0.6779 | 0.8262 | −0.1676 |
| C5' | 0.7079 | 0.8206 | −0.0827 |
| C6' | 0.7717 | 0.7548 | −0.0320 |
| C7' | 0.7645 | 0.7947 | 0.0401 |
| C8' | 0.8020 | 0.7830 | 0.1806 |
| C9' | 0.8541 | 0.7340 | 0.2498 |
| C10' | 0.9250 | 0.6495 | 0.2723 |
| C11' | 0.9448 | 0.6413 | 0.3520 |
| C12' | 0.8863 | 0.7213 | 0.3774 |
| C13' | 0.7175 | 0.8957 | 0.2530 |
| C14' | 0.5985 | 1.0362 | 0.1755 |
| C15' | 0.5372 | 1.1345 | 0.2008 |
| C16' | 0.5254 | 1.0680 | 0.2734 |
| C17' | 0.6132 | 1.0065 | 0.3137 |
| C18' | 0.6703 | 1.1143 | 0.3629 |
| C19' | 0.5995 | 0.8822 | 0.3619 |
| C20' | 0.5495 | 0.6379 | 0.3546 |
| C21' | 0.5146 | 0.5317 | 0.3061 |
| C22' | 0.4965 | 0.3964 | 0.4000 |
| C23' | 0.5305 | 0.4893 | 0.4549 |
| C24' | 0.5588 | 0.6167 | 0.4328 |
| H1A | 0.4920 | 0.6190 | −0.0283 |

TABLE 1-continued

Fractional Atomic Coordinates for the
MSA salt Form N-1 at T = RT

| Atom | X | Y | Z |
|---|---|---|---|
| H1B | 0.5447 | 0.7534 | 0.0017 |
| H1C | 0.4546 | 0.7330 | 0.0161 |
| H2A | 0.3669 | 0.7126 | 1.2479 |
| H2B | 0.4008 | 0.7592 | 1.1737 |
| H2 | −0.0822 | 0.8391 | 0.7175 |
| H3A | 0.3263 | 0.9700 | 1.1668 |
| H3B | 0.2924 | 0.9235 | 1.2410 |
| H4A | 0.2247 | 0.7284 | 1.1745 |
| H4 | 0.1280 | 0.6932 | 0.8414 |
| H6 | 0.3270 | 0.9117 | 1.0298 |
| H7 | 0.2944 | 0.8992 | 0.8773 |
| H9 | 0.1612 | 0.6330 | 1.0451 |
| H10 | 0.3207 | 1.0003 | 0.7502 |
| H11 | 0.2795 | 1.0142 | 0.6081 |
| H12 | 0.1484 | 0.8782 | 0.5588 |
| H14A | −0.0121 | 0.6199 | 0.8425 |
| H14B | 0.0516 | 0.5063 | 0.8270 |
| H15A | 0.5612 | 1.2272 | 0.2110 |
| H15B | 0.4837 | 1.1406 | 0.1621 |
| H16A | −0.1647 | 0.5926 | 0.7159 |
| H16B | −0.1580 | 0.4570 | 0.6684 |
| H18A | −0.0793 | 0.4812 | 0.5688 |
| H18B | −0.0064 | 0.4249 | 0.6367 |
| H18C | 0.0092 | 0.5558 | 0.5900 |
| H21 | −0.1051 | 1.0760 | 0.7349 |
| H23 | −0.3377 | 1.0717 | 0.5322 |
| H24 | −0.2524 | 0.8761 | 0.5548 |
| H1'1 | −0.0439 | 0.3260 | 0.0088 |
| H1'2 | 0.0470 | 0.3720 | 0.0046 |
| H1'3 | −0.0316 | 0.4661 | −0.0318 |
| H2' | 0.5758 | 0.7576 | 0.2771 |
| H2'1 | 0.7715 | 0.6937 | −0.1884 |
| H2'2 | 0.6895 | 0.7087 | −0.2622 |
| H3'1 | 0.7040 | 0.9505 | −0.2568 |
| H3'2 | 0.7861 | 0.9355 | −0.1828 |
| H4' | 0.7068 | 0.9016 | 0.1418 |
| H4" | 0.6164 | 0.8354 | −0.1886 |
| H6' | 0.8120 | 0.6952 | −0.0431 |
| H7' | 0.8598 | 0.7041 | 0.1123 |
| H9' | 0.6218 | 0.9444 | −0.0619 |
| H10' | 0.9539 | 0.6064 | 0.2403 |
| H11' | 0.9894 | 0.5911 | 0.3829 |
| H12' | 0.8853 | 0.7342 | 0.4283 |
| H14C | 0.5679 | 0.9694 | 0.1381 |
| H14D | 0.6374 | 1.0878 | 0.1531 |
| H15C | −0.0537 | 0.3676 | 0.7620 |
| H15D | −0.1071 | 0.4454 | 0.8111 |
| H16C | 0.4828 | 0.9953 | 0.2615 |
| H16D | 0.5082 | 1.1369 | 0.3058 |
| H18D | 0.7227 | 1.0712 | 0.3896 |
| H18E | 0.6426 | 1.1522 | 0.3995 |
| H18F | 0.6817 | 1.1878 | 0.3308 |
| H21' | 0.5092 | 0.5453 | 0.2540 |
| H23' | 0.5351 | 0.4696 | 0.5064 |
| H24' | 0.5828 | 0.6843 | 0.4688 |

Figure 4:
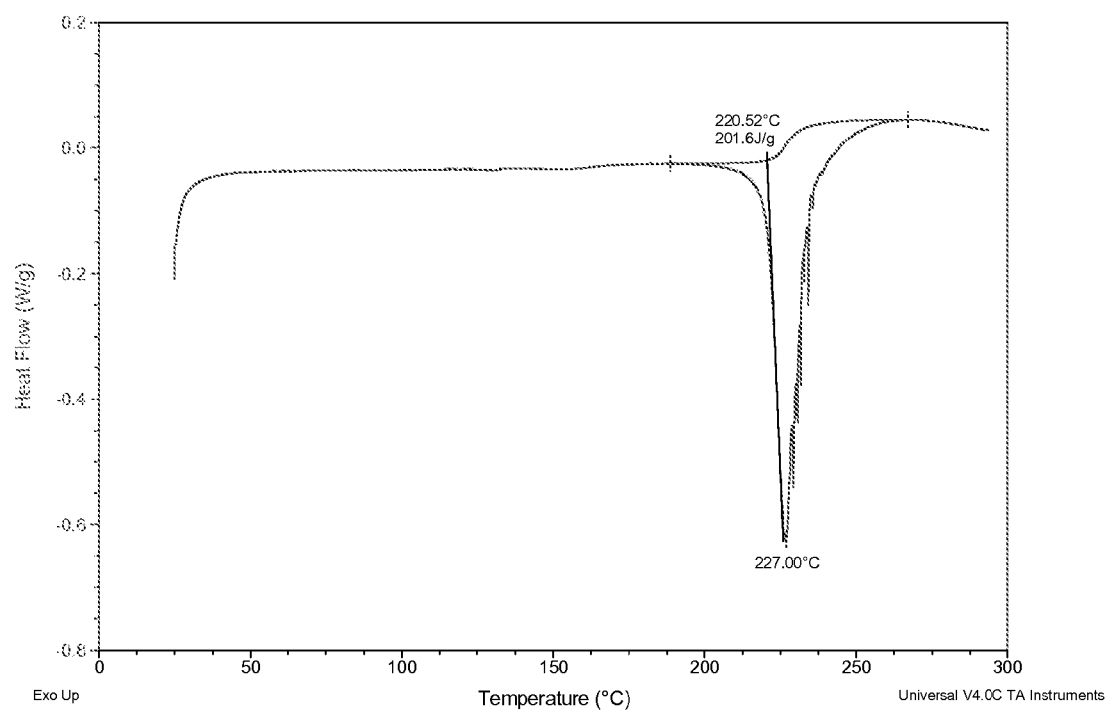
FIG. 4 shows a differential scanning calorimetry (DSC) thermogram of the N-1 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

In a still further embodiment, this form of Compound I MSA salt is characterized by a differential scanning calorimetry thermogram substantially in accordance with that shown in FIG. 4. This form may be characterized by an endotherm onset at about 205-240° C.

Figure 6:
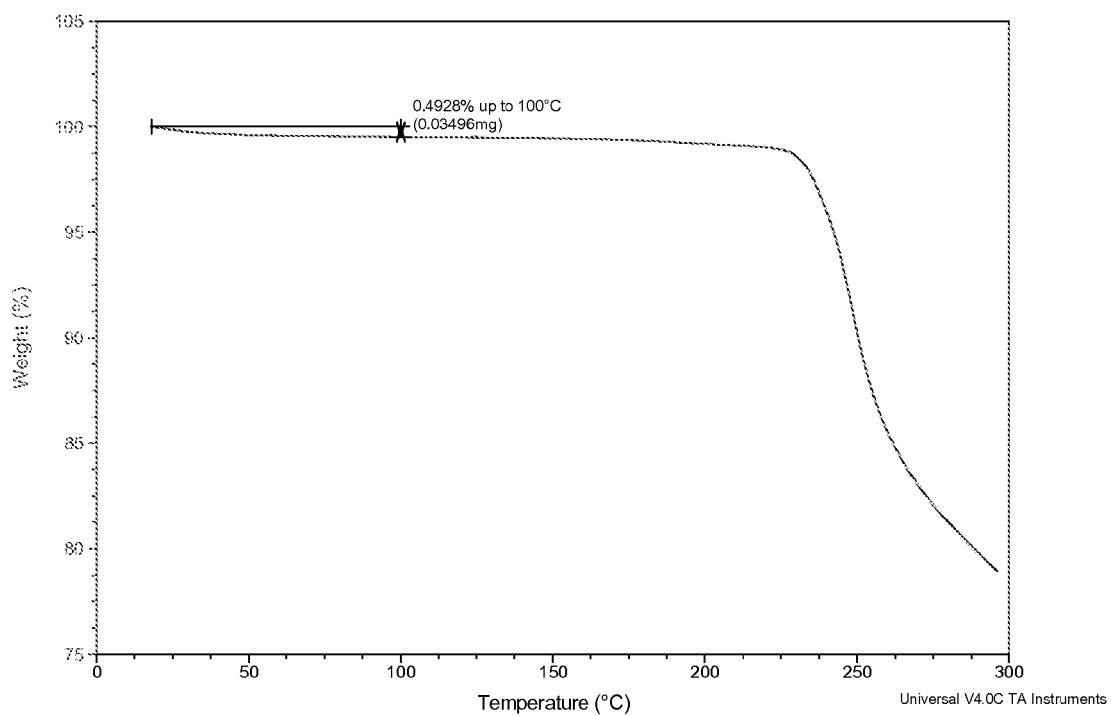
FIG. 6 shows a thermogravimetric analysis (TGA) thermogram of the N-1 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

In another embodiment, this form of Compound I MSA salt is characterized by a thermogravimetric analysis (TGA) thermogram having negligible weight loss up to a temperature of about 100° C. The invention also provides this form of Compound I MSA salt that exhibits a TGA thermogram substantially the same as shown in FIG. 6.

In still another embodiment, the N-1 Form is provided in substantially pure form. This Form of Compound I MSA salt in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-1 form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

For example, the N-1 Form may be provided in substantially pure form, wherein substantially pure is greater than 90 weight % pure, preferably greater than 95 weight % pure, and more preferably greater than 99 weight % pure.

In a different embodiment, a composition is provided consisting essentially of Form N-1 of Compound I MSA salt. The composition of this embodiment may comprise at least 90 weight %, preferably at least 95 weight %, and more preferably at least 99 weight % of the Form based on the weight of Compound I MSA salt in the composition.

The second aspect of the invention provides a neat crystalline form of Compound I MSA salt and is referred herein as the "Form N-2" or "N-2 Form".

In one embodiment, this form of Compound I MSA salt is characterized by unit cell parameters approximately equal to the following:
  Cell dimensions:
  a=16.250 Å
  b=9.576 Å
  c=34.736 Å
  α=90.0°
  β=90.0°
  γ=90.0°
  Space group: $P2_12_12_1$
  Molecules of Compound I/asymmetric unit: 2
  Volume=5405 Å$^3$
  Density (calculated)=1.370 g/cm$^3$
wherein measurement of said crystalline form is at a temperature of about −50° C.

In another embodiment, this form of Compound I MSA salt is characterized by unit cell parameters approximately equal to the following:

| Cell Parameter | Refined |
|---|---|
| a (Å) | 16.3253 |
| b (Å) | 9.5911 |
| c (Å) | 34.8200 |
| α (°) | 90 |
| β (°) | 90 |
| γ (°) | 90 |
| V (Å$^3$) | 5452.02 | wherein calculation of said crystalline form is at RT.

Figure 2:
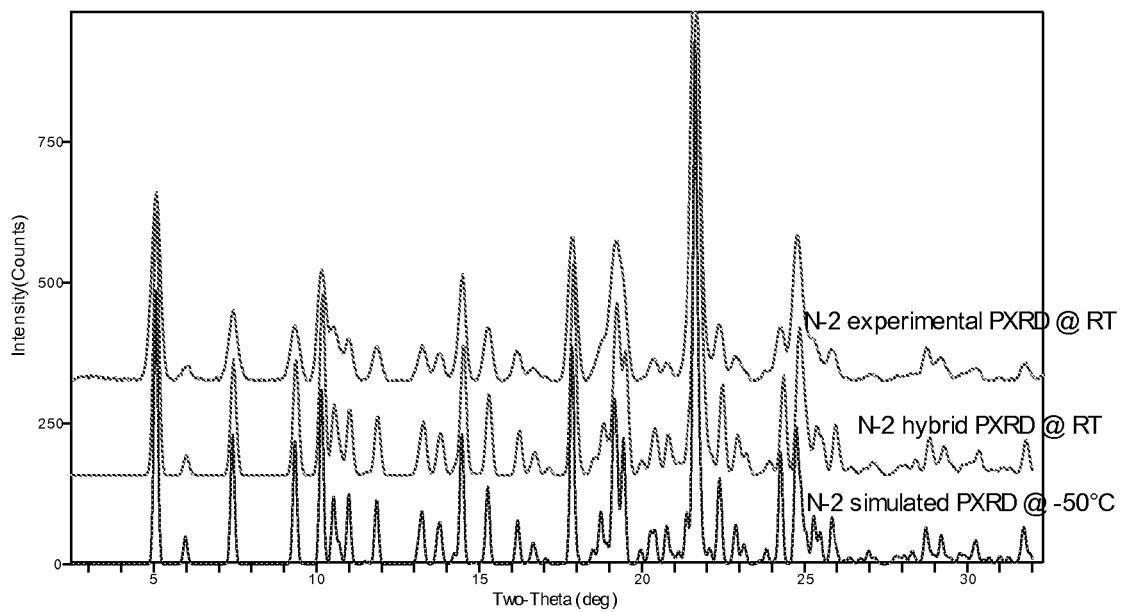
FIG. 2 shows experimental (at room temperature), hybrid (at room temperature) and simulated (at T=-50°) powder x-ray diffraction patterns (CuKα λ=1.5418 Å) of the N-2 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

In a different embodiment, this form of Compound I MSA salt is characterized by the simulated powder x-ray diffraction pattern substantially in accordance with that shown in FIG. 2 and/or by the observed powder x-ray diffraction pattern substantially in accordance with that shown in FIG. 2.

In another embodiment, there is disclosed this form of Compound I MSA salt with characteristic peaks in a powder X-ray diffraction pattern at values of 2 θ (CuKα λ=1.5418 Å at a temperature of about 25° C.) of 5.1±0.1, 6.0±0.1, 7.4±0.1, 9.3±0.1, 10.2±0.1, 10.5±0.1, 11.0±0.1, 11.8±0.1, 14.5±0.1, 15.3±0.1, 17.9±0.1, 21.6±0.1 wherein measurement of the crystalline form is at a temperature of about 25° C. Characteristic diffraction peak positions (degrees 2θ±0.1) @ RT are based on a high quality pattern collected with a diffractometer (CuKα) with a spinning capillary and 2θ calibrated with a NIST or other suitable standard.

In a further embodiment, this form of Compound IMSA salt is characterized by fractional atomic coordinates substantially as listed in Table 2.

TABLE 2

Fractional Atomic Coordinates for Form N-2 at T = –50° C.

| Atom | X | Y | Z |
|---|---|---|---|
| O1 | 0.0961 | 0.4636 | 0.0511 |
| O2 | 0.1616 | 0.6657 | 0.0757 |
| O3 | 0.2384 | 0.5005 | 0.0421 |
| S1 | 0.1600 | 0.5617 | 0.0463 |
| C45 | 0.1429 | 0.6431 | 0.0031 |
| S2 | 0.6159 | 0.4466 | 0.0512 |
| O4 | 0.6175 | 0.3471 | 0.0816 |
| O5 | 0.6763 | 0.5513 | 0.0549 |
| O6 | 0.5357 | 0.5040 | 0.0465 |
| C44 | 0.6350 | 0.3568 | 0.0094 |
| O7 | 0.1183 | 0.8633 | 0.2136 |
| F1 | –0.0142 | 0.2363 | 0.2075 |
| N1 | 0.3195 | 0.8451 | –0.0196 |
| N3A | 0.4235 | 0.7067 | 0.0579 |
| N4A | 0.3247 | 0.8267 | 0.0929 |
| N6 | 0.3111 | 0.8204 | 0.1606 |
| N8A | 0.1232 | 0.7250 | 0.1606 |
| N2 | 0.3313 | 0.8387 | 0.0183 |
| N7 | 0.2145 | 0.9316 | 0.1231 |
| N5 | 0.3817 | 0.7384 | 0.1599 |
| C1 | 0.3613 | 0.7571 | –0.0821 |
| C6 | 0.4228 | 0.6957 | 0.1263 |
| C14 | 0.1629 | 0.9716 | 0.1559 |
| C8 | 0.4185 | 0.6870 | 0.1918 |
| C5 | 0.3916 | 0.7433 | 0.0924 |
| C17 | 0.0872 | 0.6016 | 0.1762 |
| C3 | 0.4179 | 0.6951 | –0.0132 |
| N71 | 0.0326 | 0.3768 | 0.1616 |
| C11 | 0.1897 | 1.0011 | 0.0877 |
| C10 | 0.4886 | 0.6099 | 0.1392 |
| C22 | 0.0674 | 0.4988 | 0.1510 |
| C7 | 0.2859 | 0.8569 | 0.1268 |
| C4 | 0.3923 | 0.7453 | 0.0214 |
| C9 | 0.4854 | 0.6064 | 0.1783 |
| C16 | 0.1344 | 0.8469 | 0.1800 |
| C2 | 0.3691 | 0.7602 | –0.0400 |
| C13 | 0.0867 | 1.0337 | 0.1352 |
| C12 | 0.1227 | 1.1006 | 0.0991 |
| C20 | 0.0199 | 0.3615 | 0.1973 |
| C19 | 0.0389 | 0.4574 | 0.2252 |
| C15 | 0.2048 | 1.0787 | 0.1813 |
| C18 | 0.0739 | 0.5818 | 0.2138 |
| C46 | 0.4404 | 0.7664 | –0.1052 |
| C49 | 0.3949 | 0.6301 | –0.1019 |
| O8 | 0.6518 | 0.1847 | 0.2214 |
| N11 | 0.3543 | 0.3056 | 0.0581 |
| N12A | 0.4496 | 0.1937 | 0.0972 |
| N15 | 0.5573 | 0.0957 | 0.1312 |
| N16A | 0.6602 | 0.2997 | 0.1648 |
| N13 | 0.4608 | 0.2182 | 0.1644 |
| N10 | 0.4460 | 0.1631 | 0.0225 |
| N9A | 0.4567 | 0.1454 | –0.0161 |
| N14 | 0.3913 | 0.2966 | 0.1620 |
| C28 | 0.3856 | 0.2557 | 0.0237 |
| C29 | 0.3841 | 0.2796 | 0.0939 |
| C30 | 0.3511 | 0.3339 | 0.1274 |
| C39 | 0.7067 | 0.4144 | 0.1770 |
| C26 | 0.4076 | 0.2181 | –0.0382 |
| C27 | 0.3595 | 0.2913 | –0.0128 |
| C33 | 0.3519 | 0.3562 | 0.1914 |
| C37 | 0.6040 | 0.0606 | 0.1667 |
| C35 | 0.5872 | 0.0177 | 0.0972 |
| C31 | 0.2852 | 0.4233 | 0.1369 |
| C38 | 0.6384 | 0.1903 | 0.1870 |
| C36 | 0.6459 | –0.0810 | 0.1128 |
| C34 | 0.4865 | 0.1699 | 0.1317 |
| C25 | 0.4140 | 0.2091 | –0.0792 |
| C32 | 0.2846 | 0.4343 | 0.1764 |
| C23 | 0.3568 | 0.2839 | –0.1049 |
| C24 | 0.3493 | 0.1328 | –0.1015 |
| C47 | 0.5578 | –0.0295 | 0.1942 |
| C48 | 0.6782 | –0.0160 | 0.1485 |
| C50 | 0.7058 | 0.5283 | 0.1551 |
| N70 | 0.7513 | 0.6455 | 0.1629 |
| C52 | 0.7982 | 0.6378 | 0.1925 |
| C53 | 0.8083 | 0.5281 | 0.2153 |
| C54 | 0.7615 | 0.4133 | 0.2066 |
| F2 | 0.8437 | 0.7561 | 0.1986 |
| H45A | 0.1799 | 0.7207 | 0.0005 |
| H45B | 0.0871 | 0.6759 | 0.0021 |
| H45C | 0.1521 | 0.5782 | –0.0175 |
| H44A | 0.5927 | 0.2885 | –0.0055 |
| H44B | 0.6874 | 0.3109 | 0.0114 |
| H44C | 0.6357 | 0.4207 | –0.0119 |
| H98 | 0.2835 | 0.8987 | –0.0301 |
| H12N | 0.4668 | 0.6551 | 0.0581 |
| H96 | 0.3064 | 0.8611 | 0.0717 |
| H79 | 0.3121 | 0.8001 | –0.0933 |
| H8 | 0.4029 | 0.7016 | 0.2172 |
| H93 | 0.4595 | 0.6304 | –0.0177 |
| H11A | 0.1695 | 0.9338 | 0.0691 |
| H11B | 0.2357 | 1.0512 | 0.0763 |
| H10 | 0.5269 | 0.5645 | 0.1238 |
| H22 | 0.0783 | 0.5134 | 0.1251 |
| H9 | 0.5220 | 0.5580 | 0.1939 |
| H13A | 0.0475 | 0.9611 | 0.1287 |
| H13B | 0.0597 | 1.1028 | 0.1513 |
| H12A | 0.0814 | 1.1084 | 0.0789 |
| H12B | 0.1447 | 1.1926 | 0.1046 |
| H19 | 0.0285 | 0.4389 | 0.2512 |
| H15A | 0.2548 | 1.0399 | 0.1914 |
| H15B | 0.1689 | 1.1034 | 0.2022 |
| H15C | 0.2173 | 1.1604 | 0.1663 |
| H18 | 0.0879 | 0.6499 | 0.2317 |
| H46A | 0.4386 | 0.8148 | –0.1297 |
| H46B | 0.4916 | 0.7761 | –0.0911 |
| H49A | 0.3660 | 0.5965 | –0.1245 |
| H49B | 0.4190 | 0.5577 | –0.0860 |
| H80 | 0.1350 | 0.7130 | 0.1357 |
| H94 | 0.3117 | 0.3587 | 0.0567 |
| H95 | 0.4685 | 0.1531 | 0.0769 |
| H92 | 0.6443 | 0.2989 | 0.1411 |
| H90 | 0.4934 | 0.0900 | –0.0254 |
| H27 | 0.3174 | 0.3532 | –0.0190 |
| H33 | 0.3660 | 0.3480 | 0.2174 |
| H35A | 0.5422 | –0.0303 | 0.0844 |
| H35B | 0.6134 | 0.0801 | 0.0789 |
| H31 | 0.2492 | 0.4666 | 0.1198 |
| H36A | 0.6901 | –0.0975 | 0.0945 |
| H36B | 0.6194 | –0.1693 | 0.1185 |
| H32 | 0.2466 | 0.4843 | 0.1910 |
| H23A | 0.3144 | 0.3407 | –0.0931 |
| H23B | 0.3787 | 0.3209 | –0.1288 |
| H24A | 0.3670 | 0.0763 | –0.1231 |
| H24B | 0.3026 | 0.0960 | –0.0874 |
| H47A | 0.5879 | –0.0362 | 0.2180 |
| H47B | 0.5510 | –0.1209 | 0.1834 |
| H47C | 0.5047 | 0.0109 | 0.1990 |
| H48A | 0.7220 | 0.0494 | 0.1426 |
| H48B | 0.6994 | –0.0866 | 0.1658 |
| H50 | 0.6726 | 0.5284 | 0.1333 |
| H53 | 0.8450 | 0.5289 | 0.2358 |
| H54 | 0.7674 | 0.3328 | 0.2214 |
| H89 | 0.4540 | 0.2020 | –0.0900 |

Figure 5:
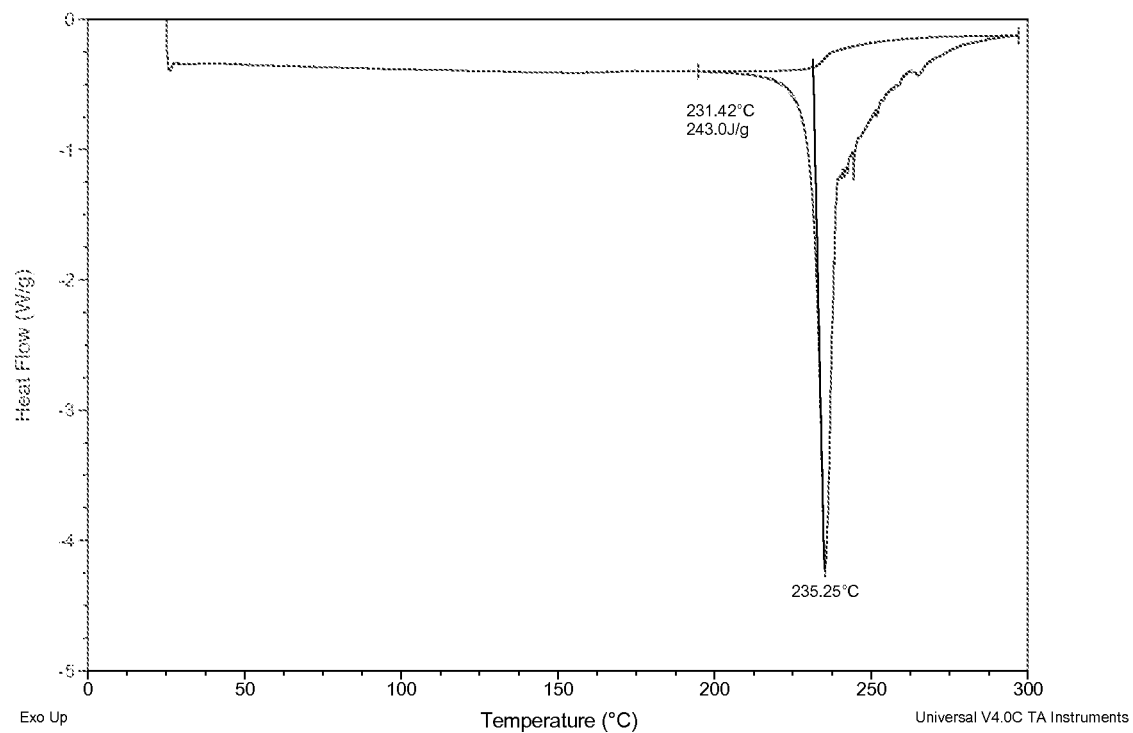
FIG. 5 shows a differential scanning calorimetry (DSC) thermogram of the N-2 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

In a still further embodiment, this form of Compound I MSA salt is characterized by a differential scanning calorimetry thermogram substantially in accordance with that shown in FIG. 5. The N-2 Form may be characterized by an endotherm onset at about 210-235° C.

Figure 7:
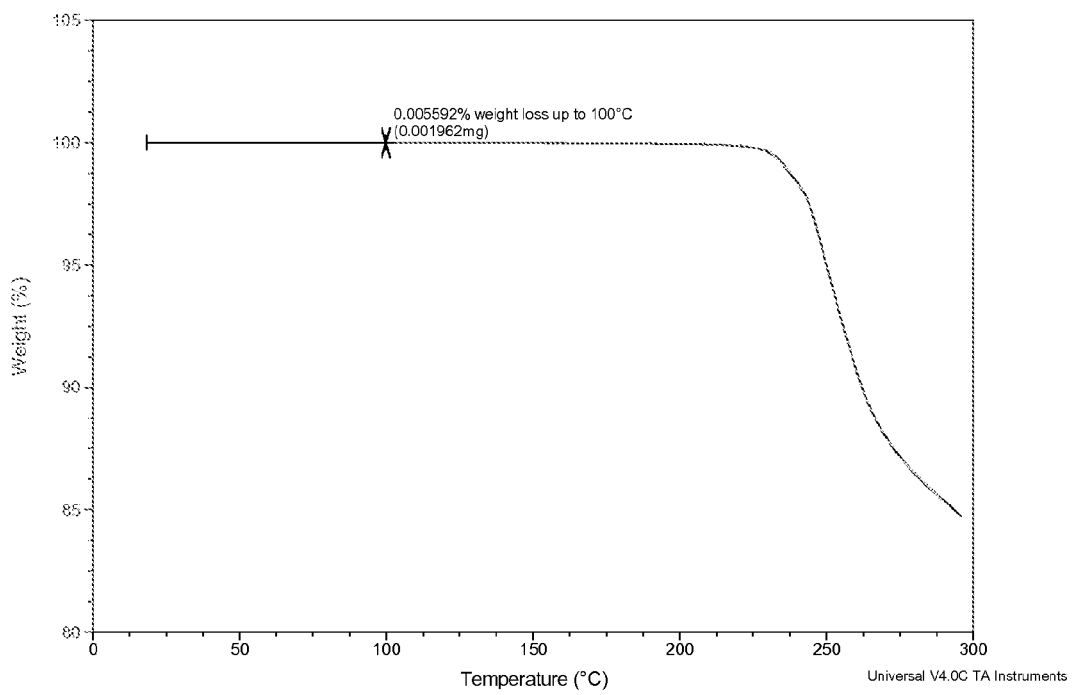
FIG. 7 shows a thermogravimetric analysis (TGA) thermogram of the N-2 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

In another embodiment, this form of Compound I MSA salt is characterized by a thermogravimetric analysis (TGA) thermogram having negligible weight loss up to a temperature of about 100° C. The invention also provides the N-2 Form of Compound I MSA salt that exhibits a TGA thermogram substantially the same as shown in FIG. 7.

In still another embodiment, this form is provided in substantially pure form. This N-2 Form of Compound I MSA salt in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-2 form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated or hybrid PXRD pattern. Most preferred is a crystalline form having substantially pure phase homogeneity with less than 1% of the total peak area in the experimentally measured PXRD pattern arising from the extra peaks that are absent from the simulated PXRD pattern.

For example, the N-2 Form may be provided in substantially pure form, wherein substantially pure is greater than 90 weight % pure, preferably greater than 95 weight % pure, and more preferably greater than 99 weight % pure.

In a different embodiment, a composition is provided consisting essentially of the Form N-2 of Compound I. The composition of this embodiment may comprise at least 90 weight %, preferably at least 95 weight %, and more preferably at least 99 weight % of the Form N-2 of Compound I, based on the weight of Compound I MSA salt in the composition.

The present invention also provides a pharmaceutical composition comprising a crystalline form of Compound I, wherein Compound I MSA salt is in Form N-1; and a pharmaceutically acceptable carrier or diluent. The pharmaceutical composition may comprise the Form N-2 in substantially pure form.

The present invention also provides a pharmaceutical composition comprising a crystalline form of Compound I MSA salt, wherein Compound I MSA salt in Form N-2; and pharmaceutically acceptable carrier or diluent. The pharmaceutical composition may comprise the Form N-2 in substantially pure form.

The present invention further provides a method for treating a proliferative disease, comprising administering to a mammalian species in need thereof, a therapeutically effective amount of Compound I, wherein Compound I MSA salt is provided in the MSA salt crystalline form comprising Form N-2 and/or Form N-1. Preferably, the mammalian species is human. The method may comprise administering Compound I, wherein Compound I MSA salt consists essentially of Form N-1. Alternatively, the method may comprise administering Compound I MSA salt, wherein Compound I MSA salt consists essentially of Form N-2.

Figure 3:
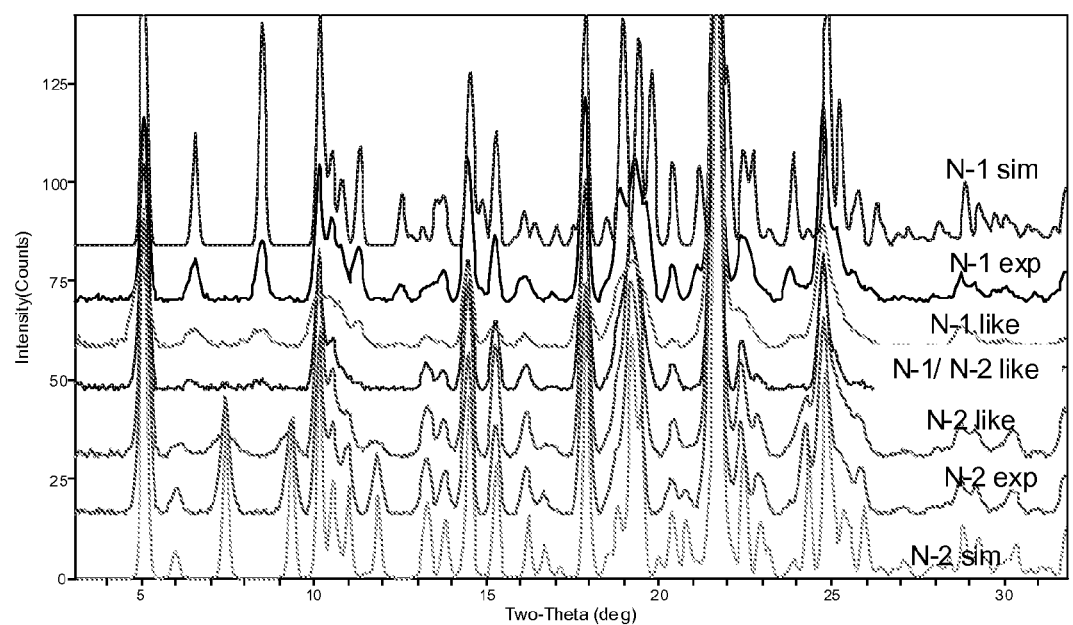
FIG. 3 shows the PXRD of the selected patterns observed of the N-1/N-2 crystalline material of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

The unit cells and crystal structures of the two polymorphic forms reported here display a number of similarities. Both forms contain dense layers of molecules with extensive hydrogen bonding/electrostatic interactions, while interactions between layers are relatively weak. The regions between layers also contain void spaces of ca. 50 Å$^3$/molecule. The PXRD patterns of the two polymorphs also similar but are easily distinguished by a few unique low angle peaks (5-10 degrees in 2-theta range); where one form has peaks the other form has none and vice versa. There are also materials with closely related patterns, which with conventional instrumentation, exhibit either very weak, or no peaks in the range 5-10 degrees of 2-theta range, but the rest of the pattern is quite similar to the two known polymorphs. Further experiments with a high power/resolution diffractometer revealed small peaks in the 5-10 degrees 2-theta with d-spacings characteristic of one or both of the two polymorphs. In fact such materials display a whole range of patterns with variable peak heights and widths in the low angle region. Based on single crystal diffraction patterns and powder pattern indexing, the observed range patterns can be understood as arising from materials containing varying amounts of layer stacking faults. Patterns with all peaks sharp correspond to very few stacking faults while patterns with severe peak broadening correspond to materials with many such faults. Although there are many "distinguishable" PXRD patterns, only two polymorphic forms of the MSA salt have been observed. The PXRD of the crystalline material N-1/N-2 is included as FIG. 3. This PXRD is not limiting as different peak intensities not specifically shown in FIG. 3 may also exist that are considered part of the invention.

Use and Utility

The crystalline forms of compound I may be used as disclosed in U.S. Pat. No. 7,534,792, which is assigned to the present assignee and is incorporated herein by reference in its entirety. In particular, the forms may be used in the treatment of diseases (such as acute myelogenous leukemia) that may be associated with signal transduction pathways operating through kinases such as Flt-3 (Fine-like kinase-3), Tie-2, CDK2, VEGFR, FGFR and IGFR kinases.

More specifically, the crystalline forms of compound I may be useful in the treatment of a variety of cancers, including (but not limited to) the following:

carcinoma, including that of the prostate, pancreatic ductal adrenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The crystalline forms of compound I may be especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleaginous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I MSA salt may also be administered sequentially with known anticancer or cytotoxic agents when a combination formulation is inappropriate. The invention is not limited in the sequence of administration; compounds of formula I MSA salt may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Typically, the solid form of a pharmaceutically active material is important in the preparation of a solid dosage form, such as tablets or capsules as the manufacturing, stability, and/or the performance of the pharmaceutically active material can be dependent upon the solid form. Generally, a crystalline form provides pharmaceutically active material with uniform properties, such as solubility, density, dissolution rate, and stability. In the present invention, the crystalline forms N-1, N-2 and N-1/N-2 of Compound I MSA salt have properties suitable for the manufacture of tablets or capsules, for providing a stable oral dosage form, and/or for delivery of the forms of Compound I MSA salt to a patient in need thereof.

Methods of Preparation and Characterization

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs,* 2nd Edition, SSCI, West Lafayette, Ind. (1999).

For crystallization techniques that employ solvent, the choice of solvent or solvents is typically dependent upon one or more factors, such as solubility of the compound, stability of the compound and crystallization technique. Solvents that are used for synthesis are often selected for ease of operation. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound in solid form to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in Mullin, J. W. et al., "Programmed Cooling of Batch Crystallizers," *Chemical Engineering Science,* 26:369-377 (1971). In general, seeds of small size are needed to control effectively the growth of crystals in the batch. Seeds of small size may be generated by sieving or by milling of large crystals. Care should be taken that milling of crystals does not result in any change in crystallinity from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, powder x-ray diffraction, or the like, to assure formation of the preferred crystalline form of the product. The resulting crystalline form may be produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound I MSA salt. This may be achieved, for example, by employing in the final process step a solvent or a mixture of solvents from which the crystalline forms of Compound I MSA salt may be crystallized. Alternatively, crystalline forms may be obtained by distillation or antisolvent addition techniques. Suitable solvents for this purpose include, for example, the aforementioned nonpolar solvents and polar solvents, including protic polar solvents such as alcohols, and aprotic polar solvents such as ketones.

The presence of more than one crystalline form and/or polymorph in a sample may be determined by techniques such as powder x-ray diffraction (PXRD) or solid state nuclear magnetic resonance (ssNMR) spectroscopy. For example, the presence of extra peaks in the comparison of an experimentally measured PXRD pattern with a simulated PXRD pattern may indicate more than one crystalline form and/or polymorph in the sample. The simulated PXRD may be calculated from single crystal x-ray data, see Smith, D. K., "A FORTRAN Program for Calculating X-Ray Powder Diffraction Patterns," Lawrence Radiation Laboratory, Livermore, Calif., UCRL-7196 (April 1963).

Crystalline forms of Compound I MSA salt according to the invention may be characterized using various techniques well known to those of ordinary skill in the art. The crystalline forms of Compound I MSA salt may be characterized and distinguished using single crystal x-ray diffraction performed under standardized operating conditions and temperatures, which is based on unit cell measurements of a single crystal of the form at a fixed analytical temperature. The approximate unit cell dimensions in Angstroms (Å), as well as the crystalline cell volume, space group, molecules per cell, and crystal density may be measured, for example at a sample temperature of 25° C. A detailed description of unit cells is provided in Stout et al., Chapter 3, *X-Ray Structure Determination: A Practical Guide*, Macmillan Co., New York (1968), which is herein incorporated by reference.

Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, preferably both run at the same analytical temperature, and measurements for the subject form characterized as a series of 2θ values (usually four or more).

Figure 8:
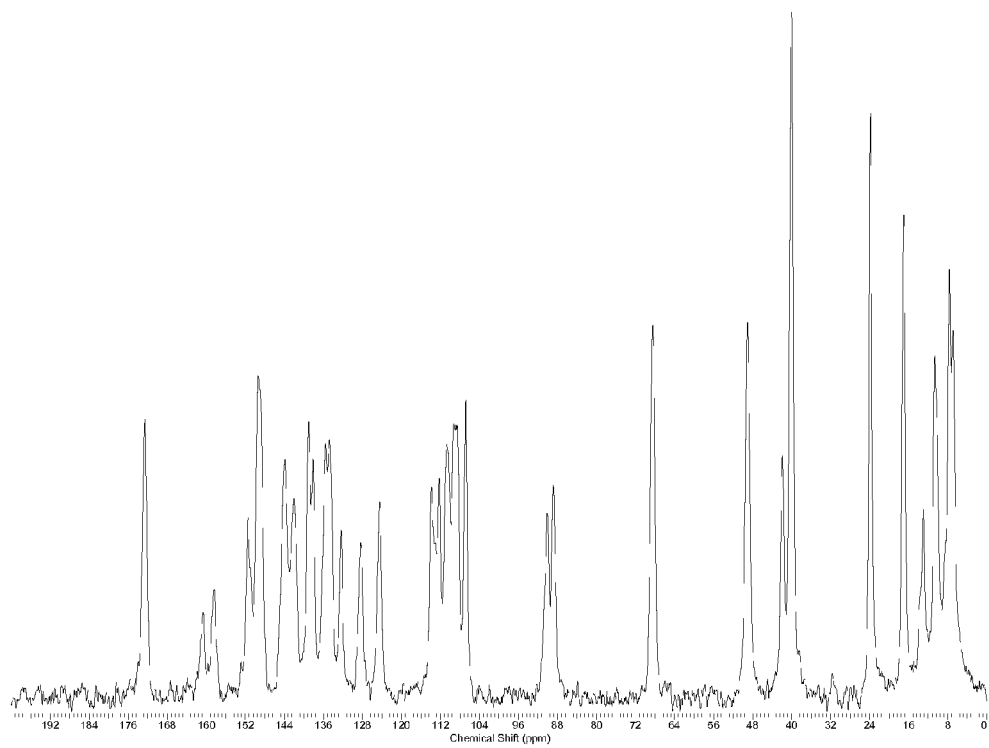
FIG. 8 shows a solid-state nuclear magnetic resonance (ssNMR) spectrum of the N-1 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.
Figure 9:
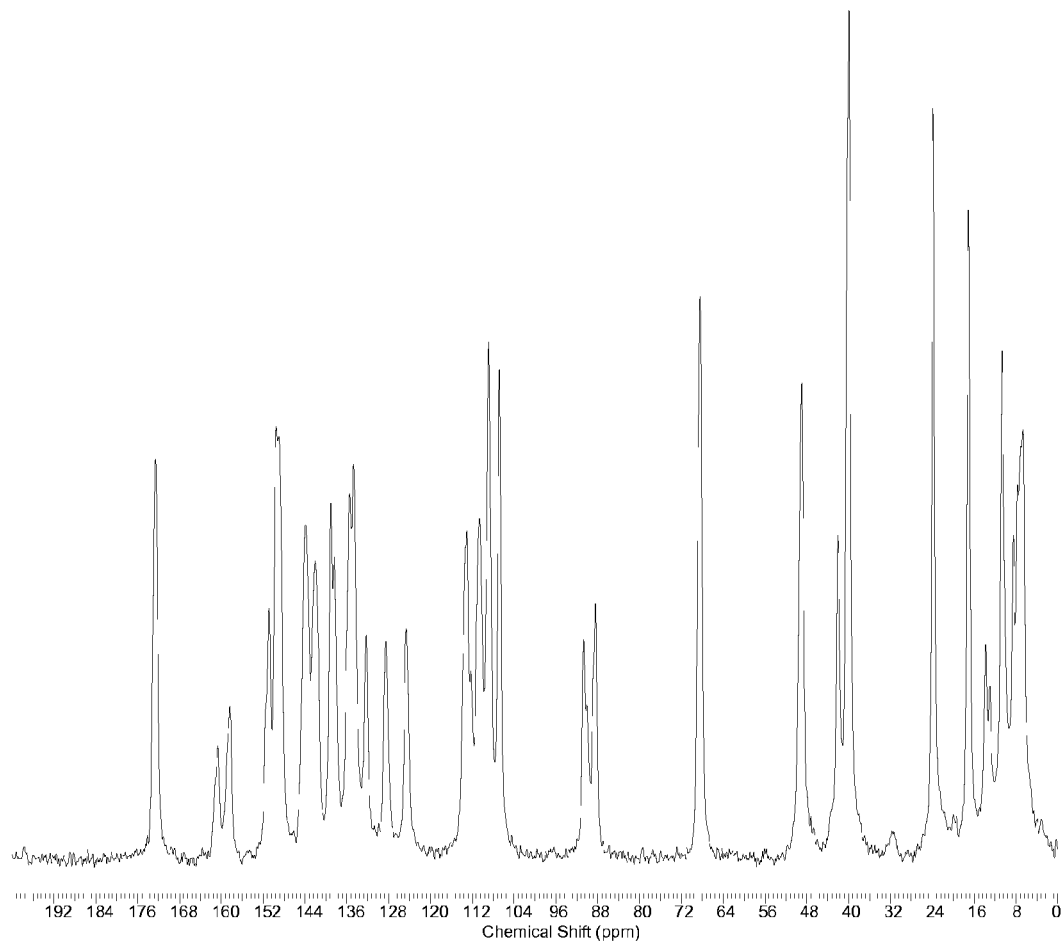
FIG. 9 shows a solid-state nuclear magnetic resonance (ssNMR) spectrum of the MSA salt of the N-2 crystalline form of (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide MSA salt.

Other means of characterizing the form may be used, such as solid-state nuclear magnetic resonance (ssNMR), differential scanning calorimetry (DSC) and thermo gravimetric analysis (TGA). These parameters may also be used in combination to characterize the subject form. ssNMR for the MSA salts Forms N-1 and N-2 are included as FIGS. 8 and 9.

The characteristic chemical shifts for the Form N-1 of the MSA salt (in ppm[1]) are as follows:

| | | | |
|---|---|---|---|
| 6.9 | 49.0 | 112.2 | 142.0 |
| 7.7 | 68.5 | 113.9 | 144.0 |
| 10.1 | 69.1 | 124.5 | 148.9 |
| 10.5 | 88.9 | 128.4 | 149.4 |
| 10.8 | 90.1 | 132.3 | 151.4 |
| 13.0 | 106.8 | 134.3 | 158.5 |
| 17.0 | 108.5 | 134.7 | 160.6 |
| 23.9 | 109.2 | 135.6 | 172.6 |
| 40.0 | 110.4 | 138.1 | |
| 41.9 | 110.8 | 139.0 | |

[1] relative to external TMS=0.0 ppm

The characteristic chemical shifts for the Form N-2 of the MSA salt (in ppm[1]) are as follows:

| | | | |
|---|---|---|---|
| 6.9 | 42.2 | 111.0 | 143.9 |
| 7.3 | 49.1 | 113.2 | 149.1 |
| 8.6 | 68.5 | 124.7 | 149.5 |
| 10.6 | 69.1 | 128.6 | 151.0 |
| 10.8 | 88.5 | 132.5 | 158.9 |
| 13.9 | 90.8 | 134.8 | 160.7 |
| 17.2 | 106.9 | 135.6 | 161.4 |
| 23.9 | 108.9 | 138.5 | 172.8 |
| 40.1 | 110.4 | 139.2 | |
| 40.4 | 110.7 | 142.2 | |

[1] relative to external TMS =0.0 ppm

The crystalline forms were analyzed using one or more of the testing methods described below.

Single Crystal X-Ray Measurements (N-1)

A Bruker SMART 2K CCD diffractometer equipped with graphite-monochromated Cu Kα radiation, (λ=1.54056 Å) was used to collect diffraction data at the room temperature. A full data set was collected using the ω scan mode over the 2θ range with a crystal-to-detector distance of 4.98 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA). The final unit cell parameters were determined using the entire data set.

All structures were solved by direct methods and refined by the full-matrix least-squares techniques, using the SHELXTL software package (Sheldrick, G. M., 1997, SHELXTL. Structure Determination Programs. Version 5.10, Bruker AXS, Madison, Wis., USA.). The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|f_c|)^2/\Sigma_w|F_o|^2]^{1/2}$, where w is an appropriate weighting function based on errors in the observed intensities. Difference FOURIER® maps were examined at all stages of refinement. All non-hydrogen atoms were refined with anisotropic thermal displacement parameters. The hydrogen atoms associated with hydrogen bonding were located in the final difference FOURIER® maps while the positions of the other hydrogen atoms were calculated from an idealized geometry with standard bond lengths and angles. They were assigned isotropic temperature factors and included in structure factor calculations with fixed parameters.

Single Crystal X-Ray Measurements (N-2)

Data were collected on a Bruker-Nonius[1] CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package[2] in the Collect program suite.[3] Alternately, single crystal data were collected on a Bruker-AXS APEX2 CCD system using Cu Kα radiation (λ=1.5418 Å). Indexing and processing of the measured intensity data were carried out with the APEX2 software package/program suite[4].

[1] BRUKER AXS, Inc., 5465 East Cheryl Parkway Madison, Wis. 53711 USA.
[2] Otwinowski, Z. et al. in *Macromolecular Crystallography*, Vol. 276, pp. 307-326, Academic, NY, publ., Carter, W. C., Jr. et al., eds. (1997).
[3] Collect Data collection and processing user interface: Collect: Data collection software, R. Hooft, Nonius B. V. (1998)
[4] APEX2 Data collection and processing user interface: APEX2 User Manual, v1.27; BRUKER AXS, Inc., 5465 East Cheryl Parkway Madison, Wis. 53711 USA.

When indicated, crystals were cooled in the cold stream of an Oxford cryo system[5] during data collection.

[5] Oxford Cryosystems Cryostream cooler: Cosier, J. et al., *J. Appl. Cryst.*, 19:105 (1986).

The structures were solved by direct methods and refined on the basis of observed reflections using either the SDP[6] software package with minor local modifications or the crystallographic packages MAXUS[7] or SHELXTL[4].

[6] SDP, Structure Determination Package, Enraf-Nonius, Bohemia N.Y. 11716. Scattering factors, including f' and f'', in the SDP software were taken from the "International Tables for Crystallography", Vol. IV, Tables 2.2A and 2.3.1, Kynoch Press, Birmingham, England (1974).
[7] maXus solution and refinement software suite: S. Mackay, C. J. Gilmore, C. Edwards, M. Tremayne, N. Stewart, K. Shankland. maXus: a computer program for the solution and refinement of crystal structures from diffraction data.

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Simulated powder x-ray diffraction patterns were generated from the single crystal atomic parameters at the data collection temperature, unless noted otherwise.

Hybrid PXRD Patterns

"Hybrid" simulated powder X-ray patterns were generated as described in the literature (Yin. S. et al., *American Pharmaceutical Review*, 6(2):80 (2003)). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected at low temperature. A new (hybrid) PXRD was calculated (by either of the software programs, Alex or LatticeView) by inserting the molecular structure determined at low temperature into the room temperature cell obtained in the first step of the procedure. The molecules are inserted in a manner that retains the size and shape of the molecule and the position of the molecules with respect to the cell origin, but, allows intermolecular distances to expand with the cell.

Powder X-Ray Diffraction Measurements

X-ray powder diffraction data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 1000 seconds. The resulting two-dimensional diffraction arcs were integrated to create a traditional 1-dimensional PXRD pattern with a step size of 0.02 degrees 2θ in the range of 3 to 35 degrees 2θ.

DSC

Differential scanning calorimetry (DSC) experiments were performed in a TA INSTRUMENTS® model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA

Thermal gravimetric analysis (TGA) experiments were performed in a TA INSTRUMENTS® model Q500 or 2950. The sample (about 7-35 mg) was placed in a platinum pan, previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

Solid-State Nuclear Magnetic Resonance (ssNMR)

All solid-state C-13 NMR measurements were made with a Bruker DSX-400, 400 MHz NMR spectrometer. High resolution spectra were obtained using a ramped cross-polarization (RAMP-CP) sequence with TPPM proton decoupling during acquisition. (Bennett, A. E. et al, *J. Chem. Phys.*, 103:6951 (1995); Metz, G. et al., *J. Magn. Reson. A*, 110:219-227 (1994)). Approximately 70 mg of sample, packed into a 4 mm canister-design zirconia rotor was used for each experiment. Chemical shifts (δ) were referenced to external adamantane with the high frequency resonance being set to 38.56 ppm (Earl, W. L. et al., *J. Magn. Reson.*, 48:35-54 (1982)).

EXAMPLES

The invention will now be further described by the following working examples, which are preferred embodiments of the invention. These examples are illustrative rather than limiting, and it is to be understood that there may be other embodiments that fall within the spirit and scope of the invention as defined by the claims appended hereto.

Crystallization Conditions for Form N-1 of Compound I MSA Salt:

Method 1:

680 mg of Compound I (free base) was dissolved in 4.0 ml ethanol. 149 mg of methanesulfonic acid (>99% purity) was dissolved in 1.0 ml ethanol. The acid solution was added to the free base solution. The resulted mixture was filtered though 0.2 μm nylon syringe filter and evaporated under a $N_2$ purged environment. The solid sample recovered was washed with excess acetonitrile and isolated by vacuum filtration to afford an off-white powder.

Method 2:

24 mg of Compound I (free base) was dissolved in 0.4 ml acetonitrile. Equimolar amount of methanesulfonic acid solution in acetonitrile (1.0M) was added to the free base solution. The resulted solution was covered and stored at ambient conditions. Solid sample crystallized out from solution within a few hours.

Crystallization Conditions for the Form N-2 of Compound I MSA Salt:

Method 1:

124 mg of Compound I (free base) was dissolved in 0.8 ml ethanol. 26 mg of methanesulfonic acid (>99% purity) was dissolved in 0.2 ml ethanol. The acid solution was added to the free base solution. The resultant solution was filtered though 0.45 μm PVDF syringe filter and slow evaporated at ambient conditions to afford the solid form.

Method 2:

An acetonitrile solution containing 1:1 mixture of Compound I (free base) and methanesulfonic acid was fast evaporated at ambient conditions to yield the solid form.

What is claimed is:

1. A crystalline form of the MSA salt of Compound I:

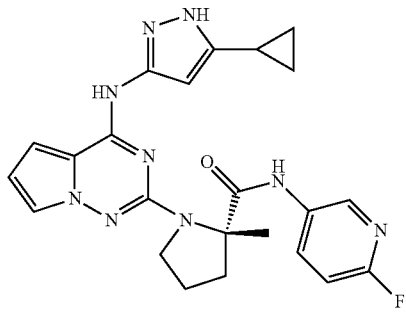

(I)

wherein said Form N-1 and/or N-2 has characteristic peaks in a powder X-ray diffraction pattern at values of 2θ of (CuKα λ=1.5418 Å): 5.1±0.1, 6.5±0.1, 8.5±0.1, 10.1±0.1, 10.5±0.1, 11.3±0.1, 14.4±0.1, 15.2±0.1, 17.8±0.1, 19.7±0.1, 21.6±0.1, wherein measurement of said crystalline form is at room temperature based on a high quality pattern collected with a diffractometer (CuKα) with a spinning capillary with 2θ calibrated with a NIST or other suitable standard.

2. A crystalline form of the MSA salt of Compound I:

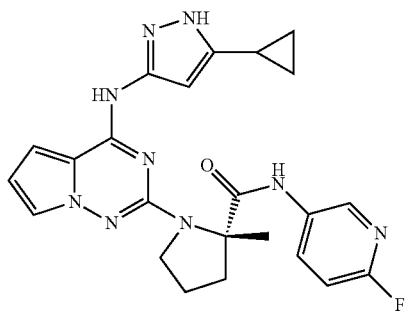

(I)

comprising Form N-1.

3. The crystalline form according to claim 2 consisting essentially of said Form N-1 of the MSA salt.

4. The crystalline form according to claim 2, wherein said Form N-1 has characteristic peaks in a powder X-ray diffraction pattern at values of 2θ of (CuKα λ=1.5418 Å): 5.1±0.1, 6.5±0.1, 8.5±0.1, 10.1±0.1, 10.5±0.1, 11.3±0.1, 14.4±0.1, 15.2±0.1, 17.8±0.1, 19.7±0.1, 21.6±0.1, wherein measurement of said crystalline form is at room temperature based on a high quality pattern collected with a diffractometer (CuKα) with a spinning capillary with 2θ calibrated with a NIST or other suitable standard.

5. The crystalline form according to claim 2, wherein said Form N-1 is characterized by the following unit cell parameters:
Cell dimensions:
a=16.3032 Å
b=9.5960 Å
c=18.0141 Å
α=90.0°
β=104.814°
γ=90.0°
Space group: P2₁
Molecules of Compound I/asymmetric unit: 2
wherein measurement of said crystalline form is at a temperature of about 25° C.

6. The crystalline form according to claim 2, wherein said Form N-1 is characterized by one or more of the following:
a) Cell dimensions:
a=16.3032 Å
b=9.5960 Å
c=18.0141 Å
α=90.0°
β=104.814°
γ=90.0°
Space group: P2₁
Molecules of Compound I/asymmetric unit: 2
wherein measurement of said crystalline form is at a temperature of about 25° C.,
b) with characteristic peaks in a powder X-ray diffraction pattern at values of 2θ of (CuKα λ=1.5418 Å) selected from: 5.1±0.1, 6.5±0.1, 8.5±0.1, 10.1±0.1, 10.5±0.1, 11.3±0.1, 14.4±0.1, 15.2±0.1, 17.8±0.1, 19.7±0.1, 21.6±0.1, wherein measurement of said crystalline form is at room temperature based on a high quality pattern collected with a diffractometer (CuKα) with a spinning capillary with 2θ calibrated with a NIST or other suitable standard; and/or
c) a thermogravimetric analysis thermogram having negligible weight loss up to a temperature of about 100° C.

7. A crystalline form of the MSA salt of Compound I:

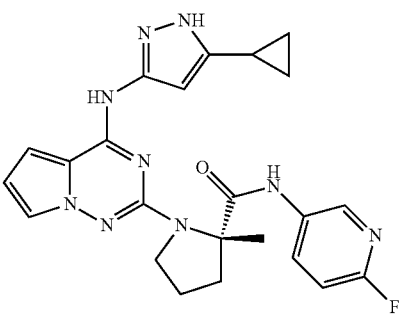

(I)

comprising Form N-2.

8. The crystalline form according to claim 7, wherein said Form N-2 has characteristic peaks in a powder X-ray diffraction pattern at values of 2θ (CuKα λ=1.5418 Å) of 5.1±0.1, 6.0±0.1, 7.4±0.1, 9.3±0.1, 10.2±0.1, 10.5±0.1, 11.0±0.1, 11.8±0.1, 14.5±0.1, 15.3±0.1, 17.9±0.1, 21.6±0.1, wherein measurement of said crystalline form is at room temperature based on a high quality pattern collected with a diffractometer (CuKα) with a spinning capillary with 2θ calibrated with a NIST or other suitable standard.

9. The crystalline form according to claim 7, wherein said Form N-2 is characterized by the following unit cell parameters:

Cell dimensions:
a=16.250 Å
b=9.576 Å
c=34.736 Å
α=90.0°
β=90.0°
γ=90.0°

Space group: $P2_12_12_1$

Molecules of Compound I/asymmetric unit: 2 wherein measurement of said crystalline form is at a temperature of about −50° C.

10. A pharmaceutical composition comprising the crystalline material according to claim 1 and a pharmaceutically acceptable carrier or diluent.

11. A pharmaceutical composition comprising the crystalline form according to claim 7 and a pharmaceutically acceptable carrier or diluent.

* * * * *